(12) United States Patent
Hamilton et al.

(10) Patent No.: US 6,514,228 B1
(45) Date of Patent: Feb. 4, 2003

(54) BALLOON CATHETER HAVING HIGH FLOW TIP

(75) Inventors: Bruce Hamilton, Hampstead, NH (US); Jane Riley, Marlborough, MA (US); Donna Lin, Trinidad, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/517,247

(22) Filed: Mar. 2, 2000

Related U.S. Application Data

(60) Provisional application No. 60/122,999, filed on Mar. 5, 1999.

(51) Int. Cl.$^7$ ............................................. A61M 29/00
(52) U.S. Cl. ............................ 604/96.01; 604/97.01; 604/102.01; 604/102.02; 604/102.03; 606/191; 606/192; 606/194
(58) Field of Search .................... 604/97.01, 96.01, 604/182, 282, 102.01, 102.02, 102.03; 606/194, 192, 191, 921, 912

(56) References Cited

U.S. PATENT DOCUMENTS

| 4,276,874 A | * | 7/1981 | Wolvek et al. ............... 128/1 D |
| 4,646,719 A |   | 3/1987 | Neuman et al. ............. 128/1 D |
| 4,744,366 A |   | 5/1988 | Jang ............................ 128/344 |
| 4,787,388 A | * | 11/1988 | Hofmann .................... 123/344 |
| 4,952,357 A | * | 8/1990 | Euteneuer ................... 264/129 |
| 4,955,895 A |   | 9/1990 | Sugiyama et al. .......... 606/191 |
| 4,958,634 A |   | 9/1990 | Jang ............................ 606/194 |
| 4,960,410 A |   | 10/1990 | Pinchuk ....................... 604/96 |
| 4,983,167 A |   | 1/1991 | Sahota ........................ 606/194 |
| 4,994,032 A |   | 2/1991 | Sugiyama et al. ............ 604/96 |
| 4,998,923 A |   | 3/1991 | Samson et al. ............. 606/194 |
| 5,002,531 A |   | 3/1991 | Bonzel ......................... 604/96 |
| 5,032,113 A | * | 7/1991 | Bruns ........................... 604/96 |
| 5,037,392 A |   | 8/1991 | Hillstead et al. ............. 604/96 |
| 5,100,385 A | * | 3/1992 | Bromander ................... 604/99 |
| 5,163,906 A |   | 11/1992 | Ahmadi ....................... 604/101 |
| 5,176,637 A |   | 1/1993 | Sagae ........................... 604/96 |
| 5,192,296 A |   | 3/1993 | Bhate et al. ................. 606/194 |
| 5,195,989 A |   | 3/1993 | Euteneuer .................... 604/280 |
| 5,242,399 A |   | 9/1993 | Lau et al. .................... 604/104 |
| 5,279,561 A | * | 1/1994 | Roucher et al. ............... 604/96 |
| 5,308,323 A |   | 5/1994 | Sogawa et al. ................ 604/95 |
| 5,328,469 A |   | 7/1994 | Coletti .......................... 604/96 |
| 5,344,413 A | * | 9/1994 | Allman et al. ............... 604/280 |
| 5,405,338 A |   | 4/1995 | Kranys ......................... 604/282 |
| 5,458,615 A |   | 10/1995 | Klemm et al. .............. 606/198 |
| 5,464,398 A |   | 11/1995 | Haindl ......................... 604/280 |
| 5,476,477 A |   | 12/1995 | Burns .......................... 606/194 |
| 5,725,545 A |   | 3/1998 | Bircoll ......................... 606/192 |
| 5,759,191 A | * | 6/1998 | Barbere ....................... 606/194 |
| 5,792,116 A |   | 8/1998 | Berg et al. .................. 604/282 |
| 5,919,145 A |   | 7/1999 | Sahatjian .................... 600/572 |
| 5,919,163 A |   | 7/1999 | Glickman .................... 604/101 |
| 6,036,697 A |   | 3/2000 | DiCaprio ..................... 606/108 |
| 6,066,157 A | * | 5/2000 | Barbere ....................... 606/194 |
| 6,179,811 B1 | * | 1/2001 | Fugoso et al. ............. 604/96.01 |
| 6,280,456 B1 | * | 8/2001 | Scribner et al. ............. 606/192 |

FOREIGN PATENT DOCUMENTS

WO wO 98/08558 3/1998

\* cited by examiner

*Primary Examiner*—Ira S. Lazarus
*Assistant Examiner*—Tu Cam Nguyen
(74) *Attorney, Agent, or Firm*—Crompton, Seager & Tufte, LLC

(57) ABSTRACT

A balloon catheter and method of use for inflating the balloon more effectively, particularly during stent deployment. The balloon catheter includes a catheter shaft and a balloon, wherein the proximal end of the balloon is connected to the distal end of the shaft. A tip is disposed in the interior of the balloon, with the proximal end of the tip extending from the distal end of the catheter shaft and the distal end of the tip connected to the distal end of the balloon. The tip includes a fluid path to facilitate the passage of inflation fluid from the inflation lumen to the interior of the balloon, and the tip may further include a guide wire lumen extending therethrough. The fluid path may be configured to inflate the balloon uniformly or to initially inflate the distal end of the balloon such that a stent loaded on the balloon will not have a tendency migrate distally during deployment. The fluid path may be defined by channel(s) in the tip, groove(s) in the tip, or by utilizing a tip having a non-circular profile.

27 Claims, 5 Drawing Sheets

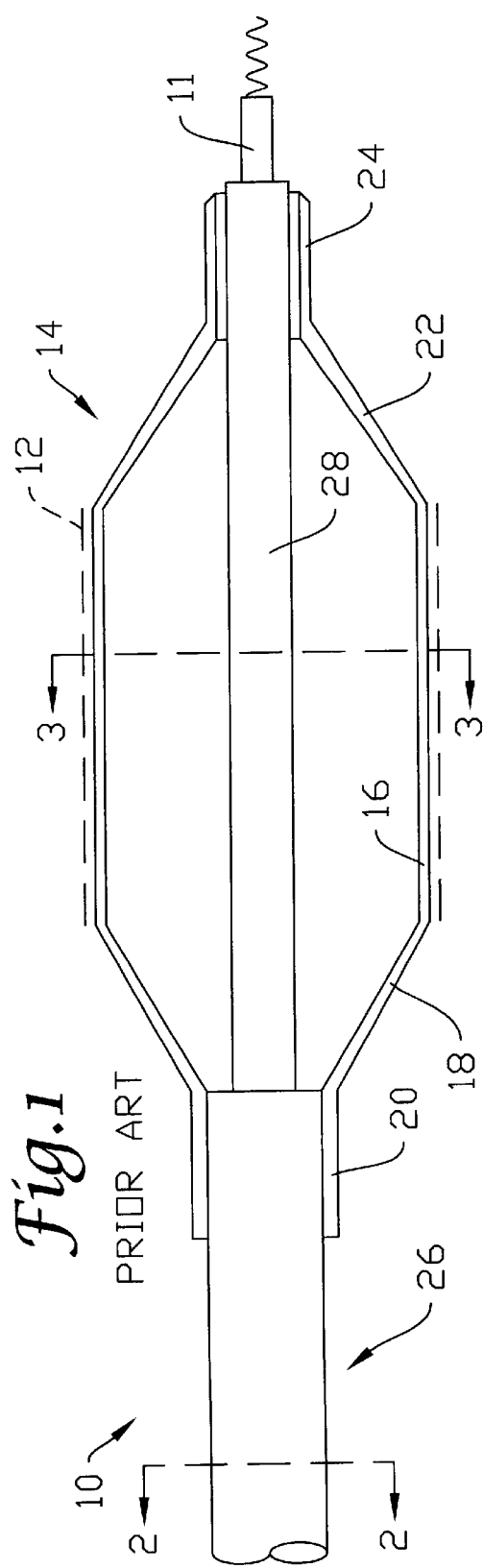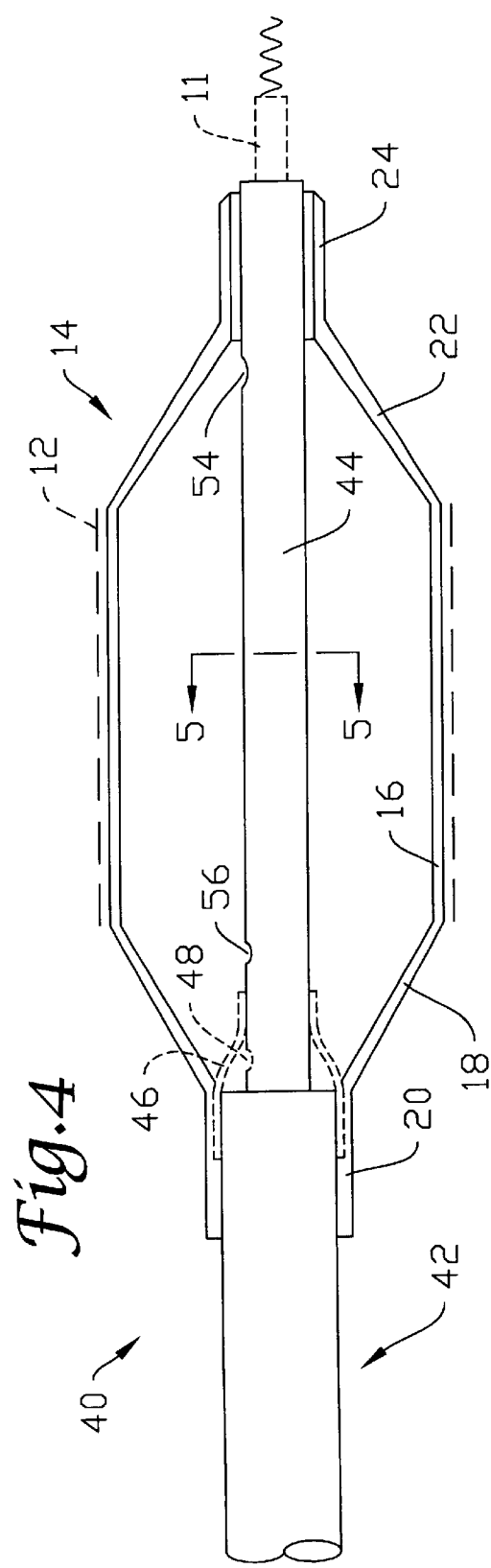

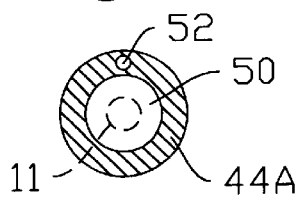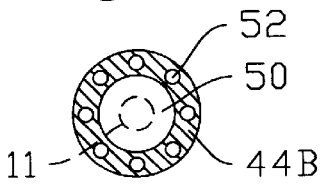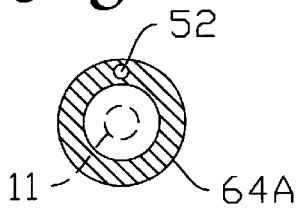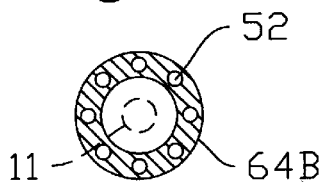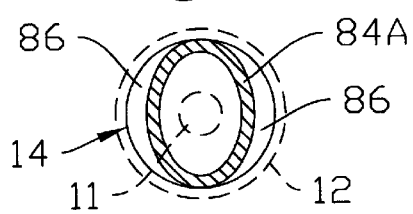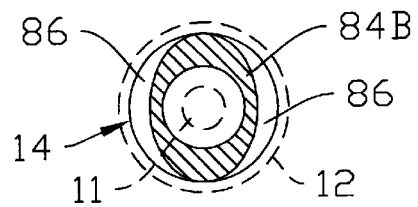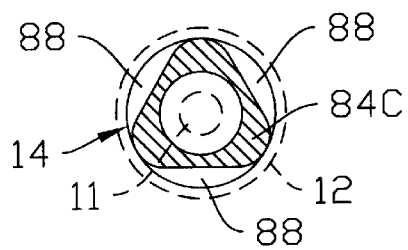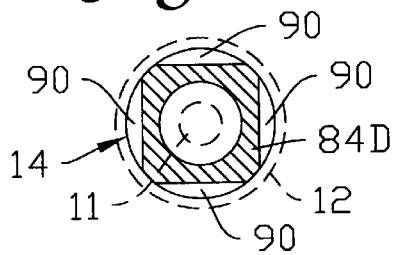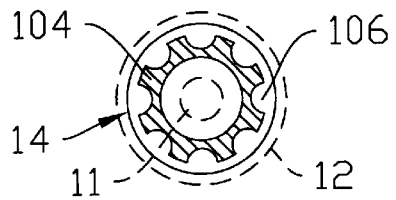

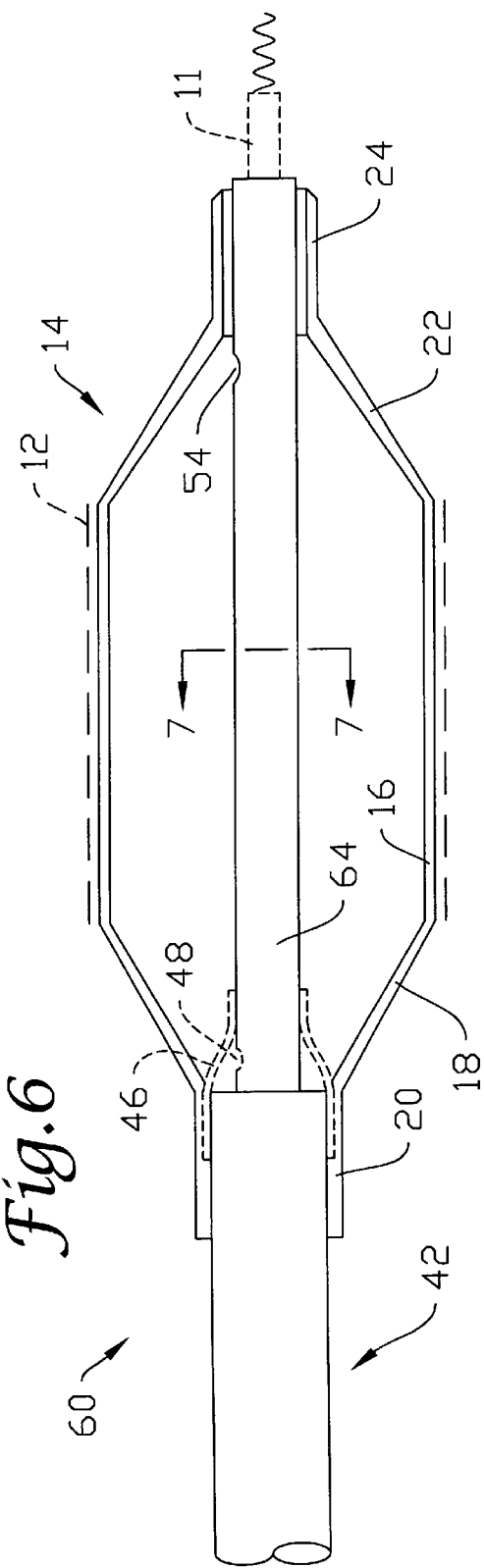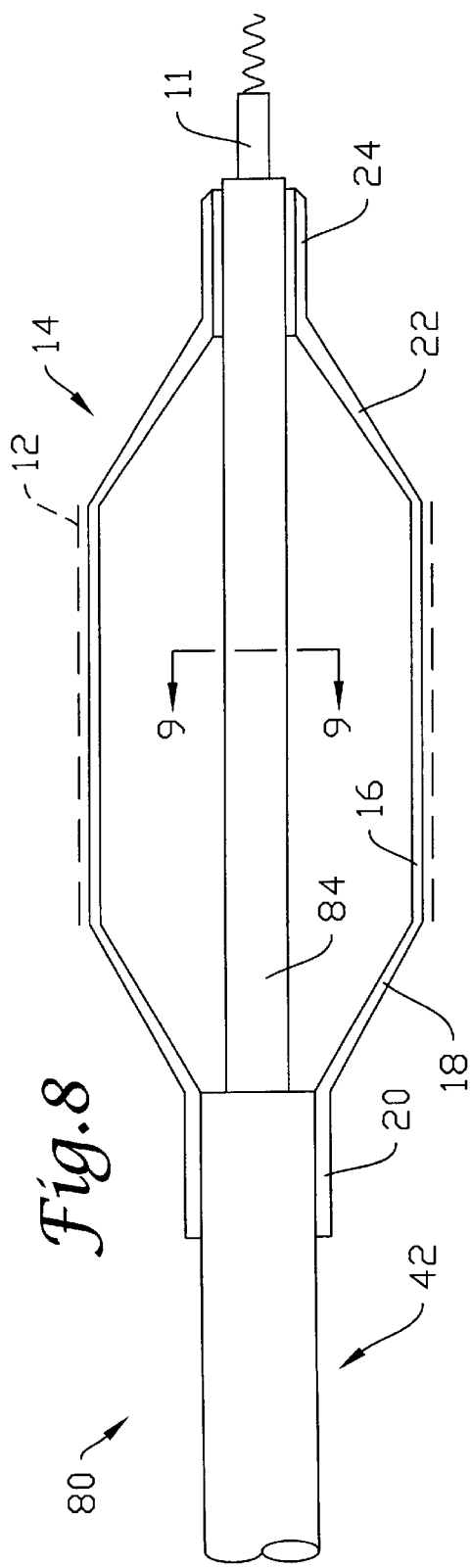

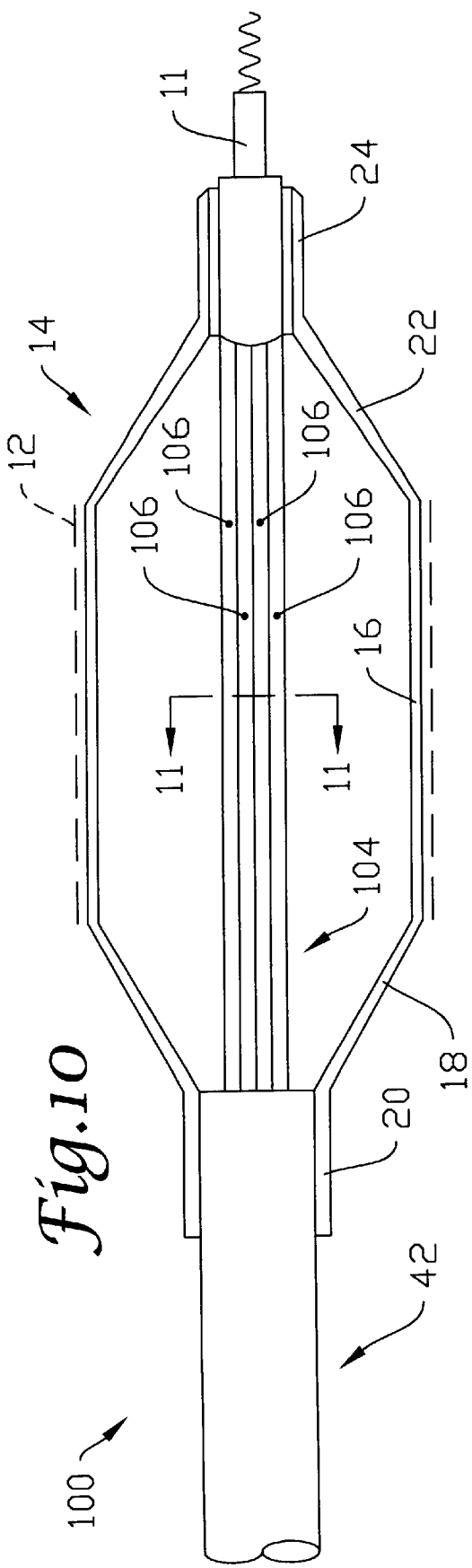

BALLOON CATHETER HAVING HIGH FLOW TIP

CROSS REFERENCES TO PROVISIONAL APPLICATION

This application claims priority to U.S. Provisional Patent Application Ser. No. 60/122,999, filed Mar. 5, 1999, entitled "HIGH FLOW TIP".

FIELD OF THE INVENTION

The present invention generally relates to intravascular balloon catheters. The present invention is particularly suited, but not limited, for application to intravascular stent delivery catheters.

BACKGROUND OF THE INVENTION

Angioplasty procedures have gained wide acceptance in recent years as an effective and safe method for treating various types of vascular disease, particularly vascular restrictions or stenoses that inhibit the flow of blood through arterial vasculature. Angioplasty procedures may be performed in virtually any part of the vascular system including the peripheral vasculature, coronary vasculature, and cerebral vasculature. The most common form of angioplasty utilizes a dilatation catheter that includes an inflatable balloon at its distal end. The catheter is percutaneously inserted into the patient's vascular system and is navigated through the vasculature to the treatment site. Typically, the treating physician utilizes an x-ray fluoroscope to guide the dilatation catheter through the vasculature and position the inflatable balloon across the restriction. Once in position, the balloon is inflated utilizing a pressure source to cause the balloon to engage and dilate the restriction, thus increasing its inside diameter and reestablishing acceptable blood flow therethrough.

Although angioplasty procedures are typically initially successful, a significant number of vascular restrictions reappear. The reappearance of a vascular restriction may be due to elastic recoil or reformation of the stenosis by smooth muscle cell proliferation (i.e., restenosis). To address this issue, treating physicians often utilize an intravascular stent to maintain the patency of the dilated restriction. A stent typically comprises a tubular structure that mechanically engages the interior wall of the vessel to maintain the inside diameter of the vessel after dilatation. The stent reduces the tendency of the vascular wall to elastically recoil after dilatation. Although some smooth muscle cell proliferation occurs around the stent to essentially embed the stent in the vascular wall, the gross dilated diameter is maintained. In this manner, the stent maintains the patency of the dilated restriction thereby maintaining adequate blood flow therethrough.

A number of stent delivery systems have been developed, typically comprising a balloon catheter having the stent mounted on the balloon. Such a deliver system may be utilized to deliver and deploy a balloon-expandable stent or a self-expanding stent. A self-expanding stent expands from its initial profile delivery diameter to its final deployed diameter by virtue of elastic forces contained in the stent structure. The balloon is then used to tack up or firmly engage the stent against the vessel wall. A balloon-expandable stent, by contrast, expands from its initial profile delivery diameter to its final deployed diameter by virtue of forces applied by the expandable balloon.

With both types of delivery systems, the stent delivery catheter is positioned such that the balloon and the stent loaded thereon extend across the dilated restriction. Once in position, the stent is deployed by either pulling back a retaining sleeve as with a self-expanding stent or by inflating the balloon as with a balloon-expandable stent. In this manner, the stent is positioned across the dilated restriction to maintain adequate blood flow therethrough.

Balloon-expandable stents have a tendency to migrate distally during deployment. The tendency of the balloon-expandable stent to migrate distally during deployment is due in part to the non-uniform inflation of the balloon. In particular, as pressurized fluid enters the balloon, the proximal end of the balloon begins to expand first. As the proximal end of the balloon expands, a longitudinal force is applied to the stent in addition to a radial force. If the longitudinal force exceeds the frictional force between the stent and the balloon surface, the stent will migrate distally. This may result in the stent being deployed in an undesirable location such as a position distal to the dilated restriction. Once the balloon-expandable stent has been deployed, it is difficult, if not impossible, to change its location. Accordingly, it is desirable to deploy the stent accurately by reducing the tendency of the balloon-expandable stent to migrate distally.

SUMMARY OF THE INVENTION

The present invention overcomes these disadvantages by providing an intravascular balloon catheter that inflates the balloon more effectively, which is particularly useful for stent delivery. For example, the balloon catheter of the present invention may be configured to inflate the balloon uniformly such that a stent loaded on the balloon will not have a tendency to migrate during deployment. Alternatively, the balloon catheter of the present invention may be configured to initially inflate the distal end of the balloon to prevent distal migration.

One embodiment of the present invention provides an intravascular balloon catheter that includes a catheter shaft and a balloon, wherein the proximal end of the balloon is connected to the distal end of the shaft. A tip is disposed in the interior of the balloon with the proximal end of the tip extending from the distal end of the catheter shaft and the distal end of the tip connected to the distal end of the balloon. The tip includes a fluid path to facilitate the passage of inflation fluid from the inflation lumen to the interior of the balloon, and the tip may further include a guide wire lumen extending therethrough. The fluid path may be configured to inflate the balloon uniformly or to initially inflate the distal end of the balloon. The fluid path may be defined by channel(s) in the tip, groove(s) in the tip, or by utilizing a tip having a non-circular profile.

BRIEF DESCRIPTION OF THE DRAWINGS

FIG. 1 is a partially cross-sectioned side view of a distal portion of a prior art stent delivery catheter for delivering a balloon-expandable stent;

FIG. 4 is a partially cross-sectioned side view of a distal portion of a balloon catheter in accordance with one embodiment of the present invention showing the balloon in an inflated state and the stent in an expanded deployed state;

FIG. 5A is a cross-sectional view taken along line 5—5 in FIG. 4 showing the balloon in a collapsed and folded state and the stent in a collapsed delivery state;

FIG. 5B is an alternative cross-sectional view taken along line 5—5 in FIG. 4 showing the balloon in a collapsed and folded state and the stent in a collapsed delivery state;

FIG. 6 is a partially cross-sectioned side view of a distal portion of a balloon catheter in accordance with another embodiment of the present invention showing the balloon in an inflated state and the stent in an expanded deployed state;

FIG. 7A is a cross-sectional view taken along line 7—7 in FIG. 6 showing the balloon in a collapsed and folded state and the stent in a collapsed delivery state;

FIG. 7B is an alternative cross-sectional view taken along line 7—7 in FIG. 6 showing the balloon in a collapsed and folded state and the stent in a collapsed delivery state;

FIG. 8 is a partially cross-sectioned side view of a distal portion of a balloon catheter in accordance with yet another embodiment of the present invention showing the balloon in an inflated state and the stent in an expanded deployed state;

FIG. 9A is a cross-sectional view taken along line 9—9 in FIG. 8 showing the balloon in a collapsed and folded state and the stent in a collapsed delivery state;

FIG. 9B is an alternative cross-sectional view taken along line 9—9 in FIG. 8 showing the balloon in a collapsed and folded state and the stent in a collapsed delivery state;

FIG. 9C is another alternative cross-sectional view taken along line 9—9 in FIG. 8 showing the balloon in a collapsed and folded state and the stent in a collapsed delivery state;

FIG. 9D is yet another alternative cross-sectional view taken along line 9—9 in FIG. 8 showing the balloon in a collapsed and folded state and the stent in a collapsed delivery state;

FIG. 10 is a partially cross-sectioned side view of a distal portion of a balloon catheter in accordance with yet another embodiment of the present invention showing the balloon in an inflated state and the stent in an expanded deployed state; and FIG. 11 is a cross-sectional view taken along line 11—11 in FIG. 10 showing the balloon in a collapsed and folded state and the stent in a collapsed delivery state.

DETAILED DESCRIPTION

Figure 2A:
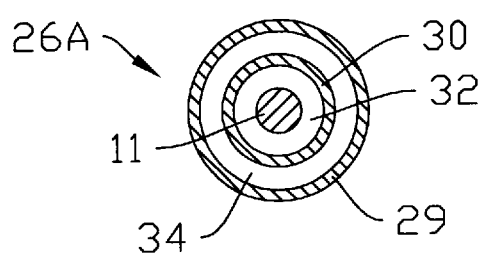
FIG. 2A is a cross-sectional view taken along line 2—2 of FIG. 1.

The following detailed description should be read with reference to the drawings in which similar elements in different drawings are numbered the same. The drawings, which are not necessarily to scale, depict selected preferred embodiments and are not intended to limit the scope or spirit of the invention.

FIG. 1 illustrates a partially cross-sectioned side view of a distal portion of a conventional over-the-wire (OTW) type balloon catheter 10. Balloon catheter 10 may be may be advanced over a conventional guide wire 11 and used as a stent delivery catheter to deliver and deploy a stent 12 (shown in phantom cross-section) mounted on the balloon 14 (shown in cross-section). Balloon 14 includes a main body portion 16, a proximal cone 18, a proximal waist 20, a distal cone 22, and a distal waist 24. The balloon 14 is mounted to the distal portion of the catheter shaft 26 and the distal tip tube 28. In particular, the proximal waist 20 of the balloon 14 is connected to the distal end of the shaft 26, and the distal waist 24 of the balloon 14 is connected to the distal end of the tip tube 28.

Figure 2B:
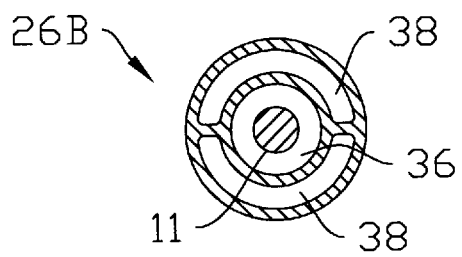
FIG. 2B is an alternative cross-sectional view taken along line 2—2 in FIG. 1.

The shaft 26 may be a coaxial type shaft 26A or a multi-lumen type shaft 26B. A coaxial type shaft 26A is illustrated in FIG. 2A, and a multi-lumen type shaft 26B is illustrated in FIG. 2B. FIGS. 2A and 2B illustrate cross-sectional views taken along line 2—2 in FIG. 1. Coaxial type shaft 26A includes an outer tube 29 and an inner tube 30. The inner tube 30 defines a guide wire lumen 32 through which the guide wire 11 extends. The annular lumen 34 defined between the inner tube 30 and the outer tube 29 is in fluid communication with the interior of the balloon 14 and functions as an inflation/deflation lumen. With this arrangement, pressurized fluid may be delivered from the proximal end (not shown) of the catheter 10 to the balloon 14 by way of the inflation lumen 34 to cause selective inflation and deflation of the balloon 14. The multi-lumen type shaft 26B may be formed by a single extrusion defining a guide wire lumen 36 and a pair of inflation lumens 38. The guide wire lumen 36 accommodates the guide wire 11 therein, and the inflation lumens 38 facilitate inflation and deflation of the balloon 14.

Figure 3A:
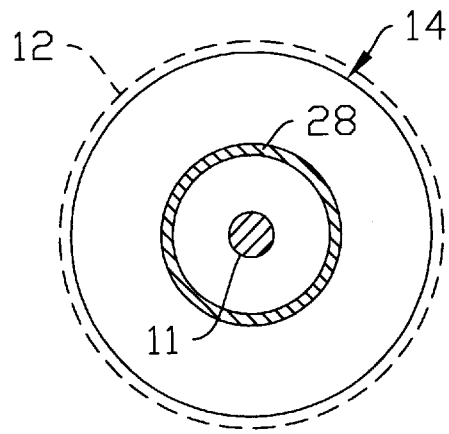
FIG. 3A is a cross-sectional view taken along line 3—3 in FIG. 1, showing the is balloon in an inflated state and the stent in an expanded deployed state.
Figure 3B:
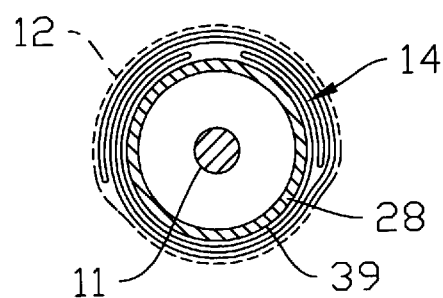
FIG. 3B is a cross-sectional view taken along line 3—3 in FIG. 1 showing the balloon in a collapsed and folded state and the stent in a collapsed delivery state.

Regardless of whether a coaxial type shaft 26A or a multi-lumen type shaft 26B is utilized, the balloon catheter 10 includes a distal tip tube 28 traversing the interior of the balloon 14, as illustrated in FIGS. 1, 3A, and 3B. FIG. 3A is a cross-sectional view taken along line 3—3 in FIG. 1, particularly illustrating the balloon 14 in the inflated state and the stent 12 (shown in phantom) in a deployed state. FIG. 3B is a cross-sectional view taken along line 3—3 in FIG. 1, particularly showing the balloon 14 in a deflated state and the stent 12 (shown in phantom) in a delivery state. As best seen in FIG. 3B, when the balloon 14 is in a deflated and folded position and the stent 12 loaded thereon (e.g., by crimping), a relatively small gap 39 is defined between the tip tube 28 and the deflated balloon 14. The relatively small gap 39 imposes a significant resistance to the flow of inflation fluid to the distal end of the balloon 14. This causes the balloon 14 to initially inflate at the proximal end thereof. When the balloon 14 is inflated, the gap 39 is gradually enlarged from the proximal end to the distal end of the balloon 14. Thus, the relatively small gap 39 prevents the uniform inflation of the balloon 14 and causes the balloon 14 to form a wedge shape during inflation.

The wedge shape that is formed as pressurized fluid enters the balloon 14 causes the balloon to exert a longitudinal force and a radial force against the stent 12. The radial force is desirable for deploying the stent 12, but the longitudinal force is undesirable. In particular, if the longitudinal force exceeds the frictional force between the stent 12 and the balloon 14 surface, the stent 12 will migrate distally. This may result in the stent 12 being deployed in an undesirable location such as a position distal to the dilated restriction. Once the balloon-expandable stent 12 has been deployed, it is difficult, if not impossible, to change its location.

All embodiments of the present invention overcome this disadvantage by providing a fluid path from the proximal end of the balloon 14 to the distal end of the balloon 14, even when the balloon is in a deflated and folded state. By providing such a fluid path, the present invention allows the balloon 14 to be inflated uniformly such that a stent 12 loaded thereon will not have a tendency to migrate distally during deployment. FIGS. 4–11 illustrate various embodiments of the present invention that provide such a fluid path. For purposes of clarity, only the distal portion of each balloon catheter of the present invention is illustrated. Those skilled in the art will recognize that many variations may be adopted for the proximal portion of the catheters of the present invention without departing from the scope and spirit of the invention. Further, because the present invention is applicable to virtually all balloon catheters, but is particularly suitable for use in an OTW stent delivery catheter, the guide wire 11 and the stent 12 are shown in phantom in FIGS. 4–11. Those skilled in the art will recognize that the present invention may be implemented into any balloon catheter having a member traversing the interior of the balloon without departing from the scope or spirit of the present invention. In particular, although described with specific reference to a balloon catheter stent delivery system, the present invention may be useful for other applications requiring uniform inflation of the balloon.

Refer now to FIG. 4, which illustrates balloon catheter 40 in accordance with one embodiment of the present invention. Except as described and illustrated herein, balloon catheter 40 is similar to balloon catheter 10. Balloon catheter 40 includes a catheter shaft 42 which may be a coaxial type shaft or a multi-lumen type shaft as described previously. A tip tube 44 extends from the distal end of the shaft 42 and may be connected thereto. In particular, if the shaft 42 is a multi-lumen extrusion, the tip tube 44 will typically be connected to the distal end of the shaft 42. If the shaft 42 is a coaxial type shaft comprising separate inner and outer tubes, the tip tube 44 will typically be connected to the inner tube. The proximal end of the balloon 14 is connected to the distal end of the shaft 42, and the distal end of the balloon 14 is connected to the distal end of the tip tube 44. A stent 12 is mounted on the balloon 14 in the conventional manner as by crimping.

As best seen in FIGS. 5A and 5B, tip tube 44 includes a guide wire lumen extension 50 and an inflation lumen extension 52. In the first embodiment illustrated in FIG. 5A, tip tube 44A utilizes one inflation lumen extension 52. A plurality of inflation lumen extensions 52 may be utilized in tip tube 44B, as illustrated in FIG. 5B. If a plurality of inflation lumen extensions 52 are utilized, a corresponding number of ports may be utilized. The inflation lumen extension(s) 52 are in fluid communication with the inflation lumen(s) 34, 38 of the shaft 42. Fluid communication may be established by a wide variety of means such as by providing connection tubes (not shown), by aligning the inflation lumen extension(s) 52 with the distal end of the inflation lumen(s) 34, 38, or by providing a transition tube 46 (shown in phantom). For purposes of illustration only, the embodiments of FIGS. 4 and 6 have been described with reference to transition tube 46. However, fluid communication between the inflation lumen extension(s) 52 and the inflation lumen(s) 34, 38 of the shaft 42 is preferably provided by alignment between the respective lumens.

If a transition tube 46 is utilized, the transition tube 46 is connected to the distal end of the shaft 42 and the proximal end of the tip tube 44 to define a fluid connection therebetween. A proximal end of the transition tube 46 may be sealingly connected between the distal end of the shaft 42 and the proximal waist 20 of the balloon 14. The distal end of the transition tube 46 may be sealingly connected to the exterior of the tip tube 44 distal of the inflation fluid entry port 48. The transition tube 46 provides a fluid path from the inflation lumen(s) 34, 38 of the shaft 42 to the inflation lumen extension(s) 52 of the tip tube 44. However, those skilled in the art will recognize that transition tube 46 is merely an example of a means for providing such a fluid path.

Inflation lumen extension(s) 52 extend from the entry port 48, past the proximal exit port 56, to the distal exit port 54. Distal exit port 54 is slightly larger that proximal exit port 56 to compensate for the pressure drop along the length of the inflation lumen extension(s) 52 extending through the tip tube 44. By utilizing a slightly larger distal exit port 54, an equal amount of inflation fluid exits through each exit port 54, 56 to uniformly inflate the balloon 14.

Pressurized inflation fluid exiting the distal end of the shaft 42 enters the proximal entry port 48 in the tip tube 44 and flows through the inflation lumen extension 52. As the inflation fluid flows through the lumen 52, inflation fluid exits through the distal exit port 54 and the proximal exit port 56, preferably in equal amounts. Inflation lumen extension 52, in combination with entry port 48 and exit ports 54, 56 defines a fluid path that enables inflation fluid to flow to the distal end of the balloon as well as the proximal end of the balloon 14. With this arrangement, the balloon 14 may be inflated uniformly, thereby expanding the stent 12 in a uniform manner. Expanding the stent 12 in a uniform manner reduces the tendency of the stent to migrate distally. Accordingly, balloon catheter 40 of the present invention permits the precise delivery and deployment of stent 12.

Refer now to FIG. 6, which illustrates a distal portion of balloon catheter 60 in accordance with another embodiment of the present invention. Except as described hereinafter, balloon catheter 60 is substantially the same as balloon catheter 40. Balloon catheter 60 includes a catheter shaft 42 and a distal tip tube 64. The proximal end of the distal tip tube 64 extends from and may be connected to the distal end of shaft 42. The distal end of the tip tube 64 is connected to the distal end of the balloon 14. Balloon 14 is connected at its proximal end to the distal end of the shaft 42. Tip tube 64 includes a proximal entry port 48 and a distal exit port 54. As compared to the tip tube 44 illustrated in FIG. 4, tip tube 64 does not include a proximal exit port. Accordingly, pressurized inflation fluid exiting the distal end of the shaft 42 enters the proximal entry port 48 and exits the distal exit port 54. Inflation lumen extension 52, in combination with entry port 48 and exit port 54, defines a fluid path that enables inflation fluid to flow to the distal end of the balloon. With this arrangement, the distal end of the balloon inflates prior to the proximal end of the balloon 14. Inflating the distal end of the balloon 14 prior to the proximal end of the balloon 14 prevents the stent 12 from sliding off the distal end of the catheter 60. Accordingly, the stent 12 is held on the catheter 60 until the balloon 14 is deflated. This allows the stent 12 to be repositioned or retrieved prior to full and complete expansion.

FIGS. 7A and 7B illustrate cross-sectional views taken along line 7—7 in FIG. 6. FIG. 7A illustrates a first embodiment of tip tube 64A having a single inflation lumen extension 52. FIG. 7B illustrates a second embodiment of tip tube 64B having a plurality of inflation lumen extensions 52. If a plurality of inflation lumen extensions 52 are utilized, a corresponding number of entry ports 48 and exits ports 54 may be used.

Refer now to FIG. 8, which illustrates a distal portion of balloon catheter 80 in accordance with yet another embodiment of the present invention. Except as described hereinafter, balloon catheter 80 is substantially the same as balloon catheter 40 illustrated in FIG. 4. Balloon catheter 80 includes a distal tip tube 84 extending from and optionally connected to the distal end of the catheter shaft 42. Balloon 14 has a proximal end connected to the distal end of the shaft 42 and a distal end connected to the distal end of the tip tube 84. In this embodiment, a transition tube is not necessary and tip tube 84 has a non-circular profile as best seen in FIGS. 9A–9D.

FIGS. 9A–9D illustrate various alternate embodiments of the tip tube 84 taken in cross-section along line 9—9 in FIG. 8. Each of the non-circular profiles of the tip tube 84 create a pathway 86 between the exterior surface of the tip tube 84 and the interior surface of the folded balloon 14. Typically, when the balloon 14 is in a folded and a collapsed state and the stent 12 is loaded thereon, the balloon 14 and the stent 12 assume a generally circular profile. As such, any non-circular profile of the tip tube 84 will result in a pathway being defined along the non-circular portion of the tip tube 84 under the collapsed balloon 14. The pathway 86 may extend along the entire length of the tip tube 84 or a portion thereof, depending on the desired position of the distal end of the pathway 86.

FIG. 9A illustrates a first embodiment of tip tube 84A having an oval outside profile and a corresponding oval inside profile to accommodate the guide wire 11. The oval profile of the tip tube 84A results in a pair of crescent-shaped lumens 86 through which inflation fluid may pass. Lumens 86 define a pathway for the flow of inflation fluid from the proximal end of the balloon 14 to the distal end of the balloon 14. FIG. 9B illustrates an alternative tip tube 84B having an oval outside profile and a circular inside profile to accommodate the guide wire 11. Having a circular inside profile allows the wall of the tip tube 84B to be thicker along the apexes of the oval. The thicker wall along the apexes allows the tip tube 84B to better retain its oval profile. Generally, the shape or profile of the guide wire lumen extension may be modified as desired without departing from the spirit of the invention.

As illustrated in FIG. 9C, tip tube 84C has a generally triangular outside profile and a circular inside profile to accommodate the guide wire 11. The triangular profile of the tip tube 84C defines three longitudinal lumens 88 which define a pathway for the flow of inflation fluid from the proximal end of the balloon 14 to the distal end of the balloon 14. FIG. 9D illustrates tip tube 84D having a generally square outside profile and a generally circular inside profile. The square outside profile of the tip tube 84D defines four crescent-shaped longitudinal lumens 90 extending along the length of the tip tube 84D to permit the passage of inflation fluid from the proximal end of the balloon 14 to the distal end of the balloon 14.

Refer now to FIG. 10, which illustrates a distal portion of balloon catheter 100 in accordance with yet another embodiment of the present invention. Balloon catheter 100 is substantially the same as balloon catheter 40 illustrated in FIG. 4, except as described hereinafter. Balloon catheter 100 includes a tip tube 104 extending from and optionally connected to the distal end of the catheter shaft 42. The proximal end of the balloon 14 is connected to the distal end of the catheter shaft 42, and the distal end of the balloon 14 is connected to the distal end of the tip tube 104. As with catheter 80 illustrated in FIG. 8, catheter 100 does not require a transition tube between the distal end of the catheter shaft 42 and the proximal end of the tip tube 104. Tip tube 104 includes a plurality of longitudinal grooves 106 extending along the length thereof The grooves 106 extend from the distal end of the catheter shaft 42 to the distal end of the balloon 14, or any point proximal thereof. The extent to which the grooves 106 extend from the distal end of the catheter shaft 42 corresponds to the portion of the balloon 14 that inflates uniformly.

Although a plurality of longitudinal grooves or channels are illustrated, any number of grooves may by utilized depending on the desired flow characteristics. Also, longitudinal, spiral, or other non-linear grooves may be used. Additionally, a variety of groove shapes may be used including U-shaped, square-shaped, rectangular-shaped, or v-shaped grooves 106. The longitudinal grooves 106 may be formed by extruding the tip tube 104 through an extrusion die having a similar profile, or by pulling an extruded tube through a reforming die having a similar profile. Further, a wide variety of grooves 106 dimensions may be used depending on the desired flow characteristics. For example, twelve or six square-shaped grooves having a depth of about 0.0045 or 0.008 inches respectively and a width of approximately 10° of the circumference may be used.

As best seen in FIG. 11, which is a cross-sectional view taken along line 11—11 in FIG. 10, when the balloon 14 is folded about the tip tube 104 and the stent 12 is loaded thereon, the channels or grooves 106 under the collapsed balloon define longitudinal pathways through which inflation fluid may pass. Grooves 106 permit the passage of inflation fluid from the proximal end of the balloon 14 to the distal end of the balloon 14, even if the balloon is folded in intimate contact with the tube 104.

Several intravascular balloon catheters 40, 60, 80, and 100 of the present invention have been described that inflate the balloon 14 more effectively, which is particularly useful for stent 12 delivery. Each catheter 40, 60, 80, and 100 may be configured to inflate the balloon 14 uniformly such that a stent 12 loaded thereon will not have a tendency to migrate during deployment. Alternatively, the balloon catheters 40, 60, 80, and 100 of the present invention may be configured to initially inflate the distal end of the balloon 14 to prevent distal migration.

Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. An intravascular balloon catheter, comprising:
a catheter shaft having a proximal end, a distal end, and an inflation lumen extending therethrough;
a balloon having a proximal end, a distal end, and an interior, the proximal end of the balloon connected to the distal end of the shaft; and
a tip disposed in the interior of the balloon, the tip having a proximal end and a distal end, the proximal end of the tip extending from the distal end of the catheter shaft and the distal end of the tip connected to the distal end of the balloon, wherein the tip includes a fluid path to facilitate the passage of inflation fluid from the inflation lumen to the interior of the balloon.

2. An intravascular balloon catheter as in claim 1, wherein the tip includes a guide wire lumen extending therethrough.

3. An intravascular balloon catheter as in claim 1, wherein the fluid path facilitates the passage of inflation fluid from the inflation lumen to the interior of the balloon adjacent the distal end of the balloon.

4. An intravascular balloon catheter as in claim 3, wherein the fluid path facilitates the passage of inflation fluid from the inflation lumen to the interior of the balloon adjacent both the proximal end and the distal end of the balloon.

5. An intravascular balloon catheter as in claim 3, wherein the fluid path is defined by a channel in the tip.

6. An intravascular balloon catheter as in claim 5, wherein the channel includes an entry port adjacent the proximal end of the tip and an exit port adjacent the distal end of the tip.

7. An intravascular balloon catheter as in claim 6, wherein the channel includes an entry port adjacent the proximal end of the tip, and a second exit port adjacent the distal end of the tip.

8. An intravascular balloon catheter as in claim 3, wherein the fluid path is defined by a plurality of channels in the tip.

9. An intravascular balloon catheter as in claim 3, wherein the tip has an exterior surface, and wherein the fluid path is defined between a groove on the exterior surface of the tip and the balloon when the balloon is in a collapsed state.

10. An intravascular balloon catheter as in claim 3, wherein the tip has an exterior surface, and wherein the fluid path is defined between a plurality of grooves on the exterior surface of the tip and the balloon when the balloon is in a collapsed state.

11. An intravascular balloon catheter as in claim 3, wherein the balloon has a substantially circular interior profile when the balloon is in a collapsed state, wherein the tip has a non-circular exterior profile, and wherein the fluid path is defined between the non-circular exterior profile of the tip and the circular interior profile of the balloon.

12. An intravascular balloon catheter as in claim 11, wherein the tip has a substantially oval profile.

13. An intravascular balloon catheter as in claim 11, wherein the tip has a substantially triangular profile.

14. An intravascular balloon catheter as in claim 11, wherein the tip has a substantially square profile.

15. A balloon catheter, comprising:
    a catheter shaft having a proximal end, a distal end, and an inflation lumen extending therethrough;
    a balloon having a proximal end, a distal end, and an interior, the proximal end of the balloon connected to the distal end of the shaft; and
    a tip disposed in the interior of the balloon, the tip having a proximal end and a distal end, the proximal end of the tip extending from the distal end of the catheter shaft and the distal end of the tip connected to the distal end of the balloon, wherein the tip includes a means for facilitating the passage of inflation fluid from the inflation lumen to the interior of the balloon.

16. A balloon catheter as in claim 15, wherein the passage means causes the balloon to initially inflate at the distal end thereof.

17. A balloon catheter as in claim 15, wherein the passage means causes the balloon to inflate substantially uniformly between the proximal and distal ends.

18. A balloon catheter as in claim 17, wherein the passage means comprises a channel in the tip.

19. A balloon catheter as in claim 17, wherein the passage means comprises a plurality of channels in the tip.

20. A balloon catheter as in claim 17, wherein the tip has an exterior surface, and wherein the passage means comprises the space defined between a groove on the exterior surface of the tip and the balloon when the balloon is in a collapsed state.

21. A balloon catheter as in claim 17, wherein the tip has an exterior surface, and wherein the passage means comprises the space defined between a plurality of grooves on the exterior surface of the tip and the balloon when the balloon is in a collapsed state.

22. A balloon catheter as in claim 17, wherein the balloon has a substantially circular interior profile when the balloon is in a collapsed state, wherein the tip has a non-circular exterior profile, and wherein the passage means comprises the space defined between the non-circular exterior profile of the tip and the circular interior profile of the balloon.

23. An intravascular balloon catheter as in claim 22, wherein the tip has a substantially oval profile.

24. An intravascular balloon catheter as in claim 22, wherein the tip has a substantially triangular profile.

25. An intravascular balloon catheter as in claim 22, wherein the tip has a substantially square profile.

26. A balloon catheter, comprising:
    a catheter shaft having a proximal end, a distal end, and an inflation lumen extending therethrough;
    a balloon having a proximal end, a distal end, and an interior, the proximal end of the balloon connected to the distal end of the shaft; and
    a tip disposed in the interior of the balloon, the tip having a proximal end and a distal end, the proximal end of the tip extending from the distal end of the catheter shaft and the distal end of the tip connected to the distal end of the balloon, wherein the tip includes a means for causing the balloon to inflate substantially uniformly between the proximal and distal ends thereof.

27. A balloon catheter, comprising: a catheter shaft having a proximal end, a distal end, and an inflation lumen extending therethrough;
    a balloon having a proximal end, a distal end, and an interior, the proximal end of the balloon connected to the distal end of the shaft; and
    a tip disposed in the interior of the balloon, the tip having a proximal end and a distal end, the proximal end of the tip extending from the distal end of the catheter shaft and the distal end of the tip connected to the distal end of the balloon, wherein the tip includes a means for causing the balloon to initially inflate at the distal end thereof.

* * * * *